(12) United States Patent
Saihata

(10) Patent No.: US 9,527,060 B2
(45) Date of Patent: Dec. 27, 2016

(54) PROCESS FOR PRODUCTION OF CATALYST FOR ALKENYL ACETATE PRODUCTION

(75) Inventor: Meiko Saihata, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 1700 days.

(21) Appl. No.: 12/377,961

(22) PCT Filed: Aug. 8, 2007

(86) PCT No.: PCT/JP2007/065874
§ 371 (c)(1),
(2), (4) Date: Feb. 18, 2009

(87) PCT Pub. No.: WO2008/029597
PCT Pub. Date: Mar. 13, 2008

(65) Prior Publication Data
US 2010/0168465 A1  Jul. 1, 2010

(30) Foreign Application Priority Data
Aug. 30, 2006  (JP) ................................ 2006-234133

(51) Int. Cl.
*C07C 67/055* (2006.01)
*B01J 31/04* (2006.01)
*B01J 23/89* (2006.01)
*B01J 23/58* (2006.01)
*B01J 37/02* (2006.01)

(52) U.S. Cl.
CPC ............. *B01J 23/8926* (2013.01); *B01J 23/58* (2013.01); *B01J 37/0203* (2013.01); *B01J 37/0205* (2013.01); *B01J 37/0207* (2013.01); *C07C 67/055* (2013.01)

(58) Field of Classification Search
None
See application file for complete search history.

(56) References Cited

U.S. PATENT DOCUMENTS

| 3,775,342 | A | 11/1973 | Kronig et al. |
| 3,822,308 | A | 7/1974 | Kronig et al. |
| 4,057,575 | A * | 11/1977 | Klass ............................ 560/245 |
| 5,347,046 | A | 9/1994 | White et al. |
| 5,808,136 | A | 9/1998 | Tacke et al. |
| 2006/0247462 | A1 | 11/2006 | Saihata et al. |

FOREIGN PATENT DOCUMENTS

| CN | 1759090 A | 2/2004 |
| EP | 0723810 A1 | 7/1996 |
| EP | 1 106 247 A2 | 6/2001 |
| JP | 49-18354 B | 5/1974 |
| JP | 8318159 A | 12/1996 |
| WO | 2004/078696 A1 | 9/2004 |

* cited by examiner

Primary Examiner — Rosalynd Keys
(74) Attorney, Agent, or Firm — Sughrue Mion, PLLC

(57) ABSTRACT

A catalyst is produced by a process that comprises at least a step of impregnating a carrier with an alkali solution having a mass of greater than 0.9 times and no greater than 1.0 times the amount of water absorption of the carrier, a step of further impregnating the carrier by contact with a solution A comprising at least a compound containing palladium or platinum and a compound containing a Group 11 element, a step of reduction treatment and a step of loading an acetic acid salt on the carrier, wherein the carrier is first impregnated with the alkali solution and then the contacted with solution A to form a catalyst precursor, and wherein the total amount of the alkali solution and solution A is a mass of at least 1.1 times and no greater than 10.0 times the amount of water absorption of the carrier. A catalyst for alkenyl acetate production is obtained that exhibits improved activity and selectivity.

9 Claims, No Drawings

PROCESS FOR PRODUCTION OF CATALYST FOR ALKENYL ACETATE PRODUCTION

TECHNICAL FIELD

The present invention relates to a process for production of a catalyst for alkenyl acetate production which is used for synthesis of alkenyl acetate from acetic acid, lower olefins and oxygen as starting materials, and to a process for production of alkenyl acetates that employs the catalyst.

BACKGROUND ART

Vinyl acetate is an important industrial material used in a wide range of fields including coatings, adhesives, fiber treatment agents and the like, as a starting material for vinyl acetate resins, as a starting material for polyvinyl alcohols, and as a monomer for copolymerization with ethylene, styrene, acrylate, methacrylate and other monomers.

Catalysts such as $Pd/Au/KOAc/SiO_2$ are commonly used for production of alkenyl acetates obtained using acetic acid, lower olefins and oxygen as starting materials, and especially vinyl acetate. The active site for the reaction is believed to be palladium, with the gold cocatalyst inhibiting sintering of the palladium, reducing carbon dioxide gas generation and improving the alkenyl acetate (for example, vinyl acetate) selectivity. It has been reported that, in order for gold to exhibit its effect, it has to mix with palladium on the atomic level.

An extremely important technical problem in the production of vinyl acetate is achieving increased vinyl acetate selectivity, while inhibition of carbon dioxide gas generation is also important from the viewpoint of the environmental load. Lengthening the life of the catalyst is another major issue for industrial production of vinyl acetate from an economical standpoint, and improving the function of gold is considered important for inhibiting sintering of palladium.

Catalysts for production of vinyl acetate which are of the "shell" type, having palladium or gold supported only on the surface of the carrier, are considered to have superior reactivity. Methods for preparation of shell-type catalysts are disclosed in Japanese Patent Public Inspection No. 2004-526553, for example. In this publication, the carrier is impregnated with a solution of the starting metal salts and then contacted with an alkali solution as a fixing agent to form a shell-type catalyst. However, this method forms a catalyst in which the positions of palladium and gold loaded in the shell are relatively separated, while the gold loading ratio is also unsatisfactorily low.

In addition, British Patent No. 1283737 and Japanese Unexamined Patent Publication No. 8-318159 disclose impregnation of carriers with alkali solutions first, followed by contact with starting metal salts solutions to form shell-type catalysts. For instance, the examples of British Patent No. 1283737 describe a step in which the carrier is impregnated with an alkali solution and the solution is then removed from the carrier by heating. Japanese Unexamined Patent Publication No. 8-318159, moreover, teaches that the total amount of the alkali solution and starting metal salts solution must be equivalent to the amount of water absorption by the carrier used. Yet the steps of these processes are complex and the preparation procedures difficult, while irregularities in loading of the palladium and gold tend to result.

Furthermore, Japanese Unexamined Patent Publication No. 10-175917 discloses treatment with a centrifugal separator after impregnation of a carrier with a starting metal salts solution for loading of the metal in a shell fashion, but the process is complex and in need of improvement.

DISCLOSURE OF THE INVENTION

It is an object of the present invention to provide a catalyst for alkenyl acetate production that exhibits improved activity and selectivity.

The present inventors have conducted much diligent research with the aim of solving the problems described above. As a result, we have discovered a catalyst preparation process that allows convenient close adjacent loading of palladium and gold. Specifically, the invention relates to the following [1]-[8].

[1] A process for production of a catalyst for alkenyl acetate production, where the catalyst consists of at least (a) a carrier, (b) palladium or platinum, (c) a Group 11 element and (d) an acetic acid salt, the process comprising:
1. a step of impregnating a carrier with an alkali solution,
2. a step of further impregnating the carrier by contact with a solution A comprising at least a compound containing palladium or platinum and a compound containing a Group 11 element,
3. a step of reduction treatment and
4. a step of loading an acetic acid salt on the carrier, and the process being characterized in that in the first step, the carrier is impregnated with an alkali solution having a mass of greater than 0.9 times and no greater than 1.0 times the amount of water absorption of the carrier, after which in the second step it is contacted with solution A to form a catalyst precursor, and in that the total amount of the alkali solution and solution A is a mass of at least 1.1 times and no greater than 10.0 times the amount of water absorption of the carrier.

[2] The process for production of a catalyst for alkenyl acetate production according to [1] above, where the catalyst consists of at least (a) a carrier, (b) palladium or platinum, (c) a Group 11 element, (d) an acetic acid salt and (e) an alkaline earth metal element, the process being characterized in that solution A further dissolves a compound containing the (e) alkaline earth metal element.

[3] The process for production of a catalyst for alkenyl acetate production according to [1] or [2] above, wherein the (b) palladium or platinum is palladium.

[4] The process for production of a catalyst for alkenyl acetate production according to any one of [1] to [3] above, wherein the (c) Group 11 element is gold or copper.

[5] The process for production of a catalyst for alkenyl acetate production according to any one of [1] to [4] above, wherein the (e) alkaline earth metal element is at least one from among barium, strontium, magnesium and calcium.

[6] A process for production of alkenyl acetates using lower olefins, oxygen and acetic acid as starting materials, the process being characterized by using a catalyst produced by a process according to any one of [1] to [5] above.

[7] A process for production of vinyl acetate using ethylene, oxygen and acetic acid as starting materials, the process being characterized by using a catalyst produced by a process according to any one of [1] to [5] above.

[8] A process for production of allyl acetate using propylene, oxygen and acetic acid as starting materials, the process being characterized by using a catalyst produced by a process according to any one of [1] to [5] above.

According to the process of the invention it is possible to conveniently produce a catalyst having palladium and gold loaded in a shell-type fashion, and improve the initial activity and selectivity of the resulting catalyst compared to conventional processes.

BEST MODE FOR CARRYING OUT THE INVENTION

Preferred modes of the invention will now be explained in detail with the understanding that the invention is not limited only to these modes, and various modifications may be implemented that are within the spirit and scope of the invention.

[Catalyst Production Step]

The catalyst for alkenyl acetate production according to the invention may be produced by a process comprising the following steps:

1. a step of impregnating a carrier with an alkali solution having a mass of greater than 0.9 times and no greater than 1.0 times the amount of water absorption of the carrier;
2. a step of impregnating the carrier with a solution A comprising a compound containing palladium or platinum, a compound containing a Group 11 element and if necessary a compound containing an alkaline earth metal element;
3. a step of reduction treatment; and
4. a step of loading an acetic acid salt onto the carrier.

According to the invention, it is important for step 1 to be followed successively by step 2 without treatment such as drying. Also, the compound containing palladium or platinum, the solution A dissolving the compound containing a Group 11 element and optionally the compound containing an alkaline earth metal element are impregnated into the carrier by contact to yield a catalyst precursor having each compound supported on the carrier, and the total mass of the alkali solution and solution A is at least 1.1 times and no greater than 10.0 times the amount of water absorption of the carrier.

Each step is preferably carried out in the order described above, although step 4 for loading of the acetic acid salt does not need to be the final step. When no alkaline earth metal element is loaded onto the carrier in step 2, the solution A will not include a compound containing an alkaline earth metal element. Other components may also be included in solution A. Other steps may also be carried out to enhance the performance of the catalyst of the invention. The reduction treatment in step 3 is for reduction of the palladium- or platinum-containing compound to palladium metal or platinum metal, and therefore it must be carried out after step 2. Each step will now be explained in detail.

1. Step of Impregnating Carrier with Alkali Solution

In this step, the carrier is impregnated with an alkali solution having a mass of greater than 0.9 times and no greater than 1.0 times the amount of water absorption of the carrier. The procedure may be carried out at ordinary temperature. As a result, the alkali solution is evenly impregnated into the carrier. Upon completion of the impregnation, the next step is carried out without drying or other procedures.

<(a) Carrier>

There are no particular restrictions on the carrier used for the invention. It may be any porous substance that is commonly used as a catalyst carrier. It is preferably silica, alumina, silica-alumina, diatomaceous earth, montmorillonite, titania or the like, and more preferably silica. When a carrier composed mainly of silica is used, the silica content of the carrier will normally be at least 50 mass % and preferably at least 90 mass % with respect to the weight of the carrier.

The carrier preferably has an specific surface area as measured by B.E.T. method which is in the range of at least 0.01 $m^2/g$, especially 10-1000 $m^2/g$ and most preferably 100-500 $m^2/g$. The water absorption is preferably 0.05-3 g/g and most preferably 0.1-2 g/g.

The water absorption of the carrier is the numerical value measured by the following method.

1. Approximately 5 g of the carrier is measured out (W1 g) and placed in a 100 cc beaker.
2. About 15 ml of purified water (ion-exchanged water) is added to the beaker to fully cover the carrier.
3. The mixture is allowed to stand for 30 minutes.
4. The carrier and purified water are poured onto wire gauze and the purified water is drained off.
5. The water adhering to the surface of the carrier is lightly pressed with a paper towel for removal until disappearance of the surface luster.
6. The weight of the carrier+purified water is measured (W2 g).
7. The water absorption of the carrier is calculated by the following formula.

$$\text{Water absorption(g/g-carrier)}=(W2-W1)/W1$$

The amount of water absorption (g) of the carrier is calculated as water absorption (g/g) of carrier×weight (g) of the carrier.

There is no particular restriction on the form of the carrier. Specifically, there may be mentioned powder, spherical and pellet forms, although there is no restriction to these.

The particle diameter of the carrier used is also not particularly restricted. It is preferably in the range of 1-10 mm and more preferably 3-8 mm. If the particle diameter is smaller than 1 mm for reaction with the catalyst packed into a tubular reactor, significant pressure loss will be experienced when the gas is passed through, potentially making it impossible to achieve effective gas circulation. Particle diameters of greater than 10 mm are not preferred, because the number of supported catalyst particles packed in the tubular reactor will be decreased, resulting in a lower total catalyst surface area and reducing the catalyst component (Pd, Au, etc.) that is distributed predominantly on the surface of the carrier. The pore structure of the carrier preferably is one with pore diameters of 1-1000 nm, and more preferably 2-800 nm.

<Alkali Solution>

The alkali solution used for the invention may be any solution which is alkaline. For example, there may be mentioned solutions of alkaline compounds such as alkali metal or alkaline earth metal hydroxides, alkali metal or alkaline earth metal bicarbonates, alkali metal or alkaline earth metal carbonates and alkali metal or alkaline earth metal silicates. As alkali metals there may be used lithium, sodium and potassium. As alkaline earth metals there may be used barium or strontium. Preferred for use are sodium metasilicate, potassium metasilicate, sodium hydroxide, potassium hydroxide, barium hydroxide and strontium hydroxide.

The alkaline compound is used in excess of the total of the (b) palladium or platinum and of the (c) Group 11 element described hereunder. For example, the alkaline compound is used at preferably 1-3 mol and more preferably 1.2-2.5 mol with respect to 1 mol of the (b) palladium or platinum. Also, it is used at preferably 2-10 mol and more preferably 3-8 mol with respect to 1 mol of the compound containing the Group 11 element (hereinafter also referred to as Group 11 element precursor).

The solvent of the alkali solution may be water, methanol, ethanol or the like. It is preferably water.

There are no particular restrictions on the method of impregnating the (a) carrier with the alkali solution, and for example, there may be mentioned (I) a method wherein the carrier is immersed for a while in a large amount of the alkali solution and then the carrier impregnated with the alkali solution in an amount equivalent to its amount of water absorption is removed, and (II) a method wherein the carrier is impregnated with a solution of the alkaline compound in a solvent which has been graduated upward to correspond to the amount of water absorption of the (a) carrier. From the viewpoint of waste liquid treatment, method (II) is preferred.

The alkali solution must be impregnated into the (a) carrier in an amount corresponding to a mass of more than 0.9 times and no greater than 1.0 times the amount of water absorption of the (a) carrier. It is more preferably used in an amount equivalent to a mass of at least 0.95 times and no greater than 1.0 times the amount of water absorption of the (a) carrier. A mass of the alkali solution of less than 0.9 times the amount of water absorption of the carrier is not preferred because it may result in loading irregularities. If the mass exceeds 1.0 times the amount of water absorption, the carrier will not be able to absorb all of the alkali solution. The amount of water absorption of the carrier is the value measured with purified water and therefore strictly speaking is different from the value for an alkali solution (aqueous alkali solution), but this value will be used for the sake of convenience.

2. Step of Impregnation of Carrier by Contact with Solution A

In this step, the carrier that has been impregnated with the alkali solution is then impregnated by contact with solution A dissolving a compound containing at least palladium or platinum and a compound containing a Group 11 element. When an alkaline earth metal element is loaded, a compound containing an alkaline earth metal element is also dissolved in solution A.

<(b) Palladium or Platinum>

The (b) palladium or platinum is the primary catalytic component, and palladium is particularly preferred from the standpoint of high vinyl acetate selectivity. The following explanation assumes palladium but applies equally to platinum.

According to the invention, the palladium may have any valency but is preferably palladium metal. ("Palladium metal" is palladium with a valency of zero.) Palladium metal can usually be obtained by reducing divalent and/or tetravalent palladium ion using a reducing agent such as hydrazine or hydrogen. It is not necessary for all of the palladium to be in the metallic state.

There are no particular restrictions on the palladium starting material, i.e. the compound containing palladium element. Palladium metal may of course be used, or a palladium salt that can be converted to palladium metal by reduction. Examples of palladium salts that can be converted to palladium metal include palladium chloride, palladium nitrate, palladium sulfate, sodium palladic chloride, potassium palladic chloride, barium palladic chloride, palladium acetate and the like, although there is no restriction to these. Sodium palladic chloride is particularly preferred for use.

There are also no particular restrictions on platinum starting materials, i.e. compounds containing platinum element. Platinum metal may of course be used, or a platinum salt that can be converted to platinum metal by reduction. Examples of platinum salts that can be converted to platinum metal include platinum chloride, platinum nitrate, platinum sulfate, sodium chloride platinate, potassium chloride platinate, barium chloride platinate, platinum acetate and the like, although there is no restriction to these.

The weight ratio of the (b) palladium or platinum and the (a) carrier is preferably (b):(a)=1:10-1000 and more preferably 1:30-500. When loading a palladium salt, for example, this is calculated as the ratio between the mass of the palladium element in the salt and the mass of the carrier.

<(c) Group 11 Element>

According to the invention, the (c) Group 11 element is an element of Group 11 of the Periodic Table according to the IUPAC Nomenclature of Inorganic Chemistry—Recommendations (1989). Specifically, this refers to gold, silver and copper, and the element is preferably gold or copper.

The (c) Group 11 element may be loaded on the carrier in the form of a compound containing the element (a Group 11 element precursor), but preferably it is in a final form of "metallic gold". ("Metallic gold" is gold with a valency of zero.) Metallic gold can usually be obtained by reducing monovalent and/or trivalent gold ion from the Group 11 element precursor using a reducing agent such as hydrazine or hydrogen. It is not necessary for all of the gold to be in the metallic state Also, there are no particular restrictions on gold or silver starting materials, i.e. compounds containing Group 11 elements. Metallic gold may of course be used, or a gold precursor that can be converted to metallic gold. As gold precursors there may be mentioned chloroauric acid, sodium chloroaurate, potassium chloroaurate and the like, among which chloroauric acid is preferred.

<(e) Alkaline Earth Metal Element>

The (e) alkaline earth metal element used for the invention may be Mg, Ca, Ba, Sr or the like, with Ba and Ca being preferred.

The alkaline earth metal element is supplied in the form of a compound containing the aforementioned elements, although there is no restriction to those compounds. A chloride, acetate, nitrate, sulfate or hydroxide of the alkaline earth metal element may be selected depending on the conditions for preparation. As particularly preferred compounds there may be mentioned $BaCl_2$, $(CH_3COO)_2Ba$, $Ba(NO_3)_2$, $Ba(OH)_2$, $CaCl_2$ and $(CH_3COO)_2Ca$.

<Solution (A)>

Solution (A) used for the invention is a solution comprising a compound containing palladium or platinum and a compound containing a Group 11 element. When an alkaline earth metal element is loaded, a compound containing an alkaline earth metal element is also dissolved therein. Other components may also be dissolved therein as necessary.

Solution A preferably comprises at least one selected from among palladic chloride, sodium palladic chloride and potassium palladic chloride and at least one selected from among chloroauric acid, sodium chloroaurate and potassium chloroaurate. When an alkaline earth metal element is also loaded, it preferably further comprises at least one selected from among barium chloride, barium acetate, barium nitrate, barium sulfate, strontium chloride, strontium acetate, strontium nitrate, strontium sulfate, magnesium chloride, magnesium acetate, magnesium nitrate, magnesium sulfate, calcium chloride, calcium acetate, calcium nitrate and calcium sulfate.

The solvent for solution A may be water, an alcohol, an organic acid, or the like. Water is preferred, from the standpoint of avoiding damage to the carrier and preventing reactivity with the compounds used.

The total mass of the alkali solution and solution A is at least 1.1 times and no greater than 10.0 times the amount of water absorption of the (a) carrier. It is more preferably a mass of 1.5-8.0 times and most preferably 2.0-6.0 times the amount of water absorption. The total mass is preferably not less than 1.1 times the amount of water absorption because the catalyst components will be unevenly loaded on the carrier. A mass of greater than 10.0 times the amount of water absorption will not affect the catalyst performance but it is not preferred because it may cause problems during production of the catalyst, such as increased waste water volume.

In the first step, a solution $A^1$ comprising a compound containing palladium or platinum, a solution $A^2$ comprising a compound containing a Group 11 element and a solution $A^3$ comprising a compound containing an alkaline earth metal element may be prepared and each solution separately impregnated into the carrier for loading of each compound on the carrier. In this case, the total amount of the alkali solution and solution A will be the total of the alkali solution, solution $A^1$, solution $A^2$ and solution $A^3$. Alternatively, solution $A^1$ and solution $A^2$ may be impregnated as a single solution (solution $A^{1+2}$) In this case, the total of the alkali solution and solution A will correspond to the sum of solution $A^{1+2}$, solution $A^3$ and the alkali solution. Other combinations of the solutions may also be calculated to determine the total of the alkali solution and solution A.

The mass of solution A is preferably 1.0-10.0 times, even more preferably 2.0-8.0 times and most preferably 2.0-5.0 times the amount of water absorption of the (a) carrier.

When solution $A^1$ is impregnated into the carrier and contacted with the alkali solution ($B^1$), and then solution $A^2$ is impregnated into the carrier and subsequently contacted with another alkali solution ($B^2$), the sum of the alkali solution $B^1$ and solution $A^1$ and the sum of the alkali solution $B^2$ and solution $A^2$ are both preferably 1.1-5 times the amount of water absorption of the carrier. When solution $A^1$ and solution $A^2$ are impregnated as a single solution (solution $A^{1+2}$), the sum of the alkali solution and solution $A^{1+2}$ is preferably 1.1-10 times the amount of water absorption of the carrier. The same applies for other combinations of the solutions. Also, the solution volume is adjusted so that the total mass of the alkali solution and solution A is in a range of at least 1.1 times and no greater than 10.0 times the amount of water absorption of the (a) carrier.

According to the invention, contact between the alkali solution-impregnated carrier and solution A causes conversion of the starting metal salt to a water-insoluble substance, to allow formation of a catalyst precursor wherein the metal component such as Pd or Au is supported in a shell-type fashion on the carrier. There are no particular restrictions on the conditions, but the contact time may be 0.5-100 hours and preferably 3-50 hours. At less than 0.5 hour, the catalyst components will not easily load in the desired amounts, and the catalyst performance may become insufficient. Contact for a period of longer than 100 hours is not preferred because the (a) carrier may suffer damage.

The contact temperature is not particularly restricted but is preferably 10-80° C. and more preferably 20-60° C. At lower than 10° C. the conversion reaction may not proceed sufficiently. At above 80° C., aggregation of the palladium and gold may occur.

3. Reduction Treatment Step

The carrier loading the compound containing palladium or platinum (palladium salt, etc.) and the Group 11 element precursor (chloroauric acid, etc.) is subjected to reduction treatment, where the compounds are preferably palladium metal and metallic gold. The reduction treatment may be liquid phase reduction or gas phase reduction.

Liquid phase reduction can be carried out in a non-aqueous system using an alcohol or hydrocarbon, or an aqueous system. The reducing agent used may be a carboxylic acid or its salt, aldehyde, hydrogen peroxide, saccharide, polyhydric phenol, diborane, amine, hydrazine or the like. Carboxylic acids and their salts include oxalic acid, potassium oxalate, formic acid, potassium formate and ammonium citrate, and glucose may be mentioned as a saccharide. As preferred reducing agents there may be mentioned hydrazine, formaldehyde, acetaldehyde, hydroquinone, sodium borohydride and potassium citrate, with the most preferred reducing agent being hydrazine.

The reducing agent used for gas phase reduction is selected from among hydrogen, carbon monoxide, alcohols, aldehydes, and olefins such as ethylene, propene and isobutene. Hydrogen, however, is preferred. An inert gas may also be added as a diluent for gas phase reduction. Examples of inert gases include helium, argon and nitrogen.

The reduction treated carrier may be washed with purified water or the like if necessary. The cleaning can be carried out either in a continuous or batch manner. The washing temperature is in the range of preferably 5-200° C. and more preferably 15-80° C., and there is no particular restriction on the cleaning time. Conditions may be selected which are sufficient for the purpose of removing residual unwanted impurities, which may include sodium and chlorine.

The reduction treated carrier may also be contacted with an acid ("acid treatment") if necessary. Contact with an acid can remove unwanted impurities, and especially with a catalyst comprising the (e) alkaline earth metal element, it can improve the catalyst performance by removing some of the excess (e) alkaline earth metal element. The acid treatment may be carried out under any conditions that permit removal of such substances. In particular, the (e) alkaline earth metal element functions to improve the dispersed state of the metal, but since undesirable secondary reactions can occur when it is present in a large amount in the catalyst, it is sometimes necessary to remove its excess.

The method of acid treatment may be one in which the carrier is immersed in an acid solution and then the acid solution is washed off by washing with water or the like. The acid used for acid treatment may be an inorganic acid such as hydrochloric acid, sulfuric acid, nitric acid, phosphoric acid or heteropolyacid, or an organic acid such as acetic acid, oxalic acid or citric acid. These acids can be selected according to the purpose described above, and may also be in the form of salts.

4. Step of Loading Acetic Acid Salt onto Carrier.

The (d) acetic acid salt is loaded by impregnating the carrier with a solution containing the necessary amount of the (d) acetic acid salt, in a mass of 0.9-1 times the amount of water absorption of the carrier. The loading may be either before or after the reduction treatment. It is preferably carried out after the reduction treatment.

<(d) Acetic Acid Salt>

The (d) acetic acid salt used for the invention is preferably at least one compound selected from among alkali metal acetates and alkaline earth metal acetates. Alkali metal acetates are particularly preferred. Specifically, there may be mentioned acetic acid salts of lithium, sodium and potassium. Preferred are sodium acetate and potassium acetate, with potassium acetate being particularly preferred.

<Catalyst Component Composition>

The weight ratio of the (b) palladium or platinum, (c) Group 11 element, (d) acetic acid salt and (e) alkaline earth metal element in the catalyst for alkenyl acetate production of the invention is preferably (b):(c):(d):(e)=1:0.001-10:0.1-100:0-100 and more preferably (b):(c):(d):(e)=1:0.1-2:0.5-20:0-30. For components (b), (c) and (e) the compositional ratio is for the masses of the elements themselves in the compounds containing each of the elements (or the mass of the metal for the metal itself), and for (d) it is for the mass of the acetic acid salt. When the catalyst does not contain component (e), the ratio of component (e) will be zero.

The starting compound for each catalyst component in solution A is prepared so that the desired catalyst composition is obtained. The concentration of the starting compound of the catalyst component in each solution may be calculated from the amount of starting compound to be loaded onto the carrier and from the amount of solution. For the actual procedure, first a prescribed amount (number of grams) of the starting compound to be loaded onto the carrier is weighed out and dissolved in the solvent, for a solution amount as specified by the invention.

The (b) palladium or platinum, (c) Group 11 element and (e) alkaline earth metal element may also be introduced into the catalyst precursor in a subsequent similar step in the form of a different solution, separate from the portion contained in solution A.

The loading amounts of the (b) palladium or platinum, (c) Group 11 element, (d) acetic acid salt and (e) alkaline earth metal element onto the (a) carrier are preferably (b) 0.001-0.05 g, (c) 0.001-0.05 g, (d) 0.01-1 g and (e) 0-0.1 g with respect to 1 g of the (a) carrier.

A catalyst obtained by the process of the invention has a shell structure (also known as "egg shell" structure) wherein most of the (b) palladium and (c) Group 11 element are supported on the surface section of the carrier. The thickness of the shell section will vary depending on the type of carrier, alkali solution and aqueous solution of the starting metal salt. When spherical silica with a diameter of 5 mm is used as the carrier, the shell section preferably has a thickness of 0.05-2 mm. The thickness is more preferably 0.1-1 mm. A thickness of less than 0.05 mm is not preferred because the activity may be reduced as a result of peeling of the carrier surface sections during the reaction. A thickness of greater than 2 mm may not provide the advantages of shell-type support.

The (d) acetic acid salt and (e) alkaline earth metal in a catalyst prepared by the process of the invention may be supported in a shell-type fashion, or they may be uniformly present throughout the catalyst.

<Specific Example of Catalyst Preparation Process>

An example of the catalyst preparation process of the invention will now be described.

Step 1: The (a) carrier is impregnated with an alkali solution in an amount equivalent to the amount of water absorption.

Step 2: The (a) carrier is immersed in a solution comprising the (b) palladium, (c) Group 11 element and (e) starting metal salt of the alkaline earth metal element in an amount graduated upward with purified water to twice the amount of water absorption of the (a) carrier, to form a catalyst precursor.

Step 3: A reducing agent is added to the solution of step 2.

Step 4: The reduced catalyst precursor is washed with purified water.

Step 5: The washed catalyst precursor is dried.

Step 6: The (d) acetic acid salt is loaded in a prescribed amount.

Step 7: Drying is performed.

[Alkenyl Acetate Production]

A process for alkenyl acetate production using a catalyst for alkenyl acetate production produced according to the invention will now be explained. The reaction for alkenyl acetate production according to the invention is preferably carried out in a gas phase using acetic acid, a lower olefin and oxygen as the reaction starting materials.

The gas phase reaction may be conducted in any manner in the prior art, but a fixed bed flow reaction is preferred.

For example, the reaction system may be the following when the lower olefin is ethylene.

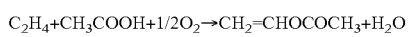

$$C_2H_4 + CH_3COOH + 1/2 O_2 \rightarrow CH_2=CHOCOCH_3 + H_2O$$

The proportion of the acetic acid, lower olefin and oxygen starting materials, in terms of molar ratio, is preferably acetic acid:lower olefin:oxygen=1:0.08-16:0.01-4, and when the lower olefin is ethylene it is preferably acetic acid:ethylene:oxygen=1:0.2-9:0.07-2. When the lower olefin is propylene it is preferably acetic acid:propylene:oxygen=1:1-12:0.5-2.

The starting gas for the reaction contains a lower olefin, acetic acid and oxygen, and if necessary nitrogen, carbon dioxide or a rare gas may be included as a diluent. If the reaction starting materials are a lower olefin, acetic acid and oxygen, the proportion between the reaction starting materials and diluent, in terms of molar ratio, is preferably reaction starting materials:diluent=1:0.05-9 and more preferably reaction starting materials:diluent=1:0.1-3.

When the reaction is conducted as a fixed bed flow reaction, the starting gas is preferably flowed through the reactor at a space velocity of 10-15,000 hr$^{-1}$ and especially 300-8000 hr$^{-1}$, under standard conditions. A space velocity of less than 10 hr$^{-1}$ may hamper removal of the heat of reaction. A space velocity of greater than 15,000 hr$^{-1}$ is not practical because it may require excessive size for the compressor or other equipment.

Water is preferably added to the starting gas at 0.5-20 mol %, and it is more preferably added at 1-18 mol %. The presence of water in the system reduces efflux of the (d) acetic acid salt from the catalyst, although the reason for this is not clearly understood. On the other hand, addition of water at more than 20 mol % will not only fail to enhance the effect but may promote hydrolysis of the alkenyl acetate, and therefore a large amount of water is not desirable.

There are no particular restrictions on the material of the reactor, but the reactor is preferably composed of a corrosion resistant material.

The reaction temperature is preferably 100-300° C. and more preferably 120-250° C. A reaction temperature of below 100° C. is not preferred because the reaction rate may be too slow. A reaction temperature of above 300° C. is also not preferred because removal of the heat of reaction may become difficult.

The reaction pressure is preferably 0-3 MPaG (gauge pressure) and more preferably 0.1-1.5 MPaG. A reaction pressure of lower than 0 MPaG is not preferred because the reaction rate may be reduced. A reaction pressure of higher than 3 MPaG is not practical because the equipment including the reaction tube will become more costly.

There are no particular restrictions on the lower olefin starting material, such as ethylene or propylene. It is generally preferred to use a high purity material, but admixture with a lower saturated hydrocarbon such as methane, ethane or propane is also satisfactory.

The oxygen to be used is also not restricted in any particular way. The oxygen may be diluted with an inert gas such as nitrogen or carbon dioxide gas, and it may be supplied as air, for example, but when the reactive gas is circulated it is advantageous to use oxygen of high concentration, and preferably 99% or greater.

When vinyl acetate is produced as the alkenyl acetate, there are no particular restrictions on the reaction temperature for production of the vinyl acetate by reaction between ethylene, oxygen and acetic acid. However, it is preferably 100-300° C. and more preferably 120-250° C. From the standpoint of equipment, it is advantageous in practice for the reaction pressure to be 0.0-3.0 MPaG, although this is not restrictive. The range is more preferably 0.1-1.5 MPaG.

The mixed gas is preferably flowed through the reactor at a space velocity of 10-15,000 hr$^{-1}$ and especially 300-8000 hr$^{-1}$, under standard conditions.

The reaction form is not particularly restricted, and any publicly known method such as using a fixed bed or fluidized bed, may be employed. Preferred for practical advantages is to employ a fixed bed prepared by packing the catalyst into a corrosion-resistant reaction tube.

The present invention will now be explained in greater detail through the following examples, with the understanding that these examples are in no way limitative on the invention.

EXAMPLE 1

Preparation of Catalyst A (Alkali Solution+Solution A at 3.0 Equivalents)

A silica spherical carrier (sphere diameter: 5 mm, specific surface area: 155 m$^2$/g, water absorption: 0.85 g/g, HSV-I by Shanghai Kaigen) was used to prepare a catalyst by the following procedure.

Step 1. A carrier (23 g, amount of water absorption: 19.7 g) was impregnated with an aqueous solution containing 2.5 g of Na$_2$SiO$_3$.9H$_2$O, in an amount equivalent to the amount of water absorption of the carrier (1 equivalent). The vessel containing the carrier and aqueous solution was gently shaken for thorough impregnation of the solution. The amount of water absorption was calculated based on a carrier weight of 23 g and an water absorption of 0.85 g/g (likewise in the following examples and comparative examples).

Step 2. The carrier obtained in step 1 was then immersed in an aqueous solution containing 1.5 g of a 56 mass % Na$_2$PdCl$_4$ aqueous solution and 1.5 g of 17 mass % HAuCl$_4$, in an amount of twice the amount of water absorption of the carrier, and was then allowed to stand for 20 hours.

Step 3. To the aqueous solution of step 2 there was added 3.3 ml of a 52 mass % hydrazine hydrate aqueous solution, and after gentle mixing, the mixture was allowed to stand at room temperature for 4 hours.

Step 4. The palladium/gold/carrier composition obtained in the previous step was rinsed with water continuously until complete elimination of chloride ion in the water after washing. The washed palladium/gold/carrier composition was dried at approximately 110° C. for 4 hours.

Step 5. The palladium/gold/carrier composition was impregnated with an aqueous solution containing 2 g of potassium acetate in an amount equivalent to the amount of water absorption of the carrier, and then dried at 110° C. for 4 hours.

EXAMPLE 2

Preparation of Catalyst B (Alkali Solution+Solution A at 3.0 Equivalents)

The procedure of Example 1 was repeated, but in Step 2. there was additionally used an aqueous solution containing 1.9 g of BaCl$_2$.2H$_2$O, in addition to the Na$_2$PdCl$_4$ and HAuCl$_4$, in an amount of twice the amount of water absorption of the carrier.

COMPARATIVE EXAMPLE 1

Preparation of Catalyst C (Prior Art Example, Alkali Solution+Solution A at 3.0 Equivalents)

A silica spherical carrier (sphere diameter: 5 mm, specific surface area: 155 m$^2$/g, water absorption: 0.85 g/g, HSV-I by Shanghai Kaigen) was used to prepare a catalyst by the following procedure.

Step 1. A carrier (23 g, amount of water absorption: 19.7 g) was impregnated with an aqueous solution containing 1.5 g of 56 mass % Na$_2$PdCl$_4$ and 1.5 g of 17 mass % HAuCl$_4$, in an amount equivalent to the amount of water absorption of the carrier (1 equivalent). The vessel containing the carrier and aqueous solution was gently shaken for thorough impregnation of the solution.

Step 2. The carrier obtained in step 1 was then immersed in an aqueous solution containing 2.5 g of Na$_2$SiO$_3$.9H$_2$O, in an amount of twice the amount of water absorption of the carrier, and was then allowed to stand for 20 hours.

Step 3. To the aqueous solution of step 2 there was added 3.3 ml of a 52 mass % hydrazine hydrate aqueous solution, and after gentle mixing, the mixture was allowed to stand at room temperature for 4 hours.

Step 4. The palladium/gold compound/carrier composition obtained in the previous step was rinsed with water continuously until complete elimination of chloride ion in the water after washing. The washed palladium/gold/carrier composition was dried at approximately 110° C. for 4 hours.

Step 5. The palladium/gold/carrier composition was impregnated with an aqueous solution containing 2 g of potassium acetate in an amount equivalent to the amount of water absorption of the carrier, and then dried at 110° C. for 4 hours.

COMPARATIVE EXAMPLE 2

Preparation of Catalyst D (Prior Art Example, Alkali Solution+Solution A at 3.0 Equivalents)

The procedure of Comparative Example 1 was repeated, but in Step 2. there was additionally used an aqueous solution containing 1.9 g of BaCl$_2$.2H$_2$O, in addition to the Na$_2$SiO$_3$.9H$_2$O, in an amount of twice the amount of water absorption of the carrier.

EXAMPLE 3

Preparation of Catalyst E (Alkali Solution+Solution A at 3.0 Equivalents, with Acid Treatment)

The procedure of Example 2 was repeated, but the following steps were carried out between step 4 and step 5.

Step E-1. The palladium/gold/barium/carrier composition obtained in step 4 was immersed for 1 hour in a 0.45 mass % acetic acid aqueous solution in an amount corresponding to three times the amount of water absorption.

Step E-2. The palladium/gold/barium/carrier composition obtained in step E-1 was continuously washed with water for one night.

Step E-3. the palladium/gold/barium/carrier composition obtained in step E-2 was dried at approximately 110° C. for 4 hours.

EXAMPLE 4

Preparation of Catalyst F (Alkali Solution+Solution A at 3.0 Equivalents)

A silica spherical carrier (sphere diameter: 5 mm, specific surface area: 155 m$^2$/g, water absorption: 0.85 g/g, HSV-I by Shanghai Kaigen) was used to prepare a catalyst by the following procedure.

Step 1. A carrier (23 g, amount of water absorption: 19.7 g) was impregnated with an aqueous solution containing 2.5 g of $Na_2SiO_3.9H_2O$, in an amount of 0.95 times the amount of water absorption of the carrier. The vessel containing the carrier and aqueous solution was gently shaken for thorough impregnation of the solution.

Step 2. The carrier obtained in step 1 was then immersed in an aqueous solution containing 1.5 g of a 56 mass % $Na_2PdCl_4$ aqueous solution, 1.5 g of 17 mass % $HAuCl_4$ and 1.9 g of $BaCl_2.2H_2O$, in an amount of twice the amount of water absorption of the carrier, and was then allowed to stand for 20 hours.

Step 3. After then adding 0.5 g of potassium citrate to the aqueous solution of step 2, it was gently mixed and allowed to stand at room temperature for 4 hours.

Step 4. The palladium/gold/barium compound/carrier composition obtained in the previous step was washed with water until complete elimination of chloride ion in the water after washing. The washed palladium/gold/carrier composition was dried at approximately 110° C. for 4 hours.

Step 5. The palladium/gold/barium compound/carrier composition was impregnated with an aqueous solution containing 2 g of potassium acetate, in an amount equivalent to the amount of water absorption of the carrier, and then dried at 110° C. for 4 hours.

EXAMPLE 5

Preparation of Catalyst G (Alkali Solution+Solution A at 3.0 Equivalents)

The procedure of Example 1 was repeated but the 1.5 g of 17 mass % $HAuCl_4$ in Step 2. was changed to 1.6 g of 17 mass % $NaAuCl_4$.

EXAMPLE 6

Preparation of Catalyst H (Alkali Solution+Solution a at 3.0 Equivalents)

A silica spherical carrier (sphere diameter: 5 mm, specific surface area: 155 m$^2$/g, water absorption: 0.85 g/g, HSV-I by Shanghai Kaigen) was used to prepare a catalyst by the following procedure.

Step 1. A carrier (23 g, amount of water absorption: 19.7 g) was impregnated with an aqueous solution containing 0.52 g of potassium hydroxide, in an amount equivalent to the amount of water absorption of the carrier (1 equivalent). The vessel containing the carrier and aqueous solution was gently shaken for thorough impregnation of the solution.

Step 2. The carrier obtained in step 1 was then immersed in an aqueous solution containing 1.5 g of a 56 mass % $Na_2PdCl_4$ aqueous solution, 1.5 g of 17 mass % $HAuCl_4$ and 1.9 g of $BaCl_2.2H_2O$, in an amount of twice the amount of water absorption of the carrier, and was then allowed to stand for 20 hours.

Step 3. To the aqueous solution of step 2 there was added 3.3 ml of a 52 mass % hydrazine hydrate aqueous solution, and after gentle mixing, the mixture was allowed to stand at room temperature for 4 hours.

Step 4. The palladium/gold/barium compound/carrier composition obtained in the previous step was washed with water until complete elimination of chloride ion in the water after washing. The washed palladium/gold/carrier composition was dried at approximately 110° C. for 4 hours.

Step 5. The palladium/gold/barium compound/carrier composition was impregnated with an aqueous solution containing 2 g of potassium acetate in an amount equivalent to the amount of water absorption of the carrier, and then dried at 110° C. for 4 hours.

COMPARATIVE EXAMPLE 3

Preparation of Catalyst I (Alkali Solution+Solution A at 1.0 Equivalent)

A silica spherical carrier (sphere diameter: 5 mm, specific surface area: 155 m$^2$/g, water absorption: 0.85 g/g, HSV-I by Shanghai Kaigen) was used to prepare a catalyst by the following procedure.

Step 1. A carrier (23 g, amount of water absorption: 19.7 g) was impregnated with an aqueous solution containing 2.5 g of $Na_2SiO_3.9H_2O$, in an amount of 0.5 times the amount of water absorption of the carrier. The vessel containing the carrier and aqueous solution was gently shaken for thorough impregnation of the solution.

Step 2. The carrier obtained in step 1 was then immersed in an aqueous solution containing 1.5 g of a 56 mass % $Na_2PdCl_4$ aqueous solution and 1.5 g of 17 mass % $HAuCl_4$, in an amount of 0.5 times the amount of water absorption of the carrier, and was then allowed to stand for 20 hours.

Step 3. To the aqueous solution of step 2 there was added 3.3 ml of a 52 mass % hydrazine hydrate aqueous solution, and after gentle mixing, the mixture was allowed to stand at room temperature for 4 hours.

Step 4. The palladium/gold/carrier composition obtained in the previous step was washed with water continuously until complete elimination of chloride ion in the water after washing. The washed palladium/gold/carrier composition was dried at approximately 110° C. for 4 hours.

Step 5. The palladium/gold/carrier composition was impregnated with an aqueous solution containing 2 g of potassium acetate, in an amount corresponding to the amount of water absorption of the carrier, and then dried at 110° C. for 4 hours.

COMPARATIVE EXAMPLE 4

Preparation of Catalyst J (Alkali Solution+Solution A at 3.0 Equivalents, Dried Once)

A silica spherical carrier (sphere diameter: 5 mm, specific surface area: 155 m$^2$/g, water absorption: 0.85 g/g, HSV-I by Shanghai Kaigen) was used to prepare a catalyst by the following procedure.

Step 1. A carrier (23 g, amount of water absorption: 19.7 g) was impregnated with an aqueous solution containing 2.5 g of $Na_2SiO_3 \cdot 9H_2O$, in an amount equivalent to the amount of water absorption of the carrier (1 equivalent). The vessel containing the carrier and aqueous solution was gently shaken for thorough impregnation of the solution.

Step 2. The carrier obtained in step 1 was dried in air at 110° C. for 4 hours.

Step 3. The carrier obtained in step 2 was then immersed in an aqueous solution containing 1.5 g of a 56 mass % $Na_2PdCl_4$ aqueous solution and 1.5 g of 17 mass % $HAuCl_4$, in an amount of twice the amount of water absorption of the carrier, and was then allowed to stand for 20 hours.

Step 4. To the aqueous solution of step 3 there was added 3.3 ml of a 52 mass % hydrazine hydrate aqueous solution, and after gentle mixing, the mixture was allowed to stand at room temperature for 4 hours.

Step 5. The palladium/gold/carrier composition obtained in the previous step was washed with water continuously until complete elimination of chloride ion in the water after washing. The washed palladium/gold/carrier composition was dried at approximately 110° C. for 4 hours.

Step 6. The palladium/gold/carrier composition was impregnated with an aqueous solution containing 2 g of potassium acetate, in an amount corresponding to the amount of water absorption of the carrier, and then dried at 110° C. for 4 hours.

COMPARATIVE EXAMPLE 5

Preparation of Catalyst K

The procedure of Comparative Example 1 was repeated, except for using an aqueous solution further containing 0.50 g of $CaCl_2$, in an amount of twice the amount of water absorption of the carrier in Step 2.

COMPARATIVE EXAMPLE 6

Preparation of Catalyst L

The procedure of Comparative Example 1 was repeated, except for using an aqueous solution further containing 0.91 g of $MgCl_2 \cdot 6H_2O$, in an amount of twice the amount of water absorption of the carrier in Step 2.

EXAMPLE 7

Preparation of Catalyst M

The procedure of Example 1 was repeated, except for using an aqueous solution further containing 0.50 g of $CaCl_2$, in an amount of twice the amount of water absorption of the carrier in Step 2.

EXAMPLE 8

Preparation of Catalyst N

The procedure of Example 1 was repeated, except for using an aqueous solution further containing 0.91 g of $MgCl_2 \cdot 6H_2O$, in an amount of twice the amount of water absorption of the carrier in Step 2.

EXAMPLE 9

Preparation of Catalyst O

The procedure of Example 2 was repeated, but the following steps were carried out between step 4 and step 5.

Step O-1. Water containing 9 g of silicotungstic acid, in an amount equivalent to the amount of water absorption, was loaded by impregnation into the palladium/gold/barium compound/carrier composition obtained in step 4.

Step O-2. The palladium/gold/barium/silicotungstic acid/carrier composition obtained in step O-1 was continuously washed with water overnight.

Step E-3. The palladium/gold/barium/silicotungstic acid/carrier composition obtained in step O-2 was dried at approximately 110° C. for 4 hours.

COMPARATIVE EXAMPLE 7

Preparation of Catalyst P

The procedure of Comparative Example 2 was repeated, but the following steps were carried out between step 4 and step 5.

Step P-1. The palladium/gold/barium/carrier composition obtained in step 4 was immersed for 1 hour in a 0.45 mass % acetic acid aqueous solution in an amount corresponding to three times the amount of water absorption.

Step P-2. The palladium/gold/barium/carrier composition obtained in step P-1 was continuously washed with water for one night.

Step P-3. The palladium/gold/barium/carrier composition obtained in step P-2 was dried at approximately 110° C. for 4 hours.

[Catalyst Evaluation]
Measurement of Metal Loading Weight

A 3 g loaded catalyst sample was pulverized and pressed into a disc with an inner diameter of 3 cm. The metal weight of the disc was measured using a PW2404 fluorescent X-ray analysis device by Philips.

Measurement of Metal Surface Area

This was measured by CO pulse adsorption using an R6015 by Ohkura Riken, Inc.

Initial Catalytic Activity Evaluation Test A

After diluting 3 cc of the catalyst with 75 cc of glass beads, it was packed into a reaction tube (SUS316 L, inner diameter: 22 mm, length: 480 mm). Reaction was conducted with a reaction temperature of 150° C., a reaction pressure of 0.6 MPaG, and with circulation of gas with a gas composition of $C_2H_4/O_2/H_2O/HOAc/N_2$=47.3/6.1/5.6/26.3/14.7 (mol %) at a flow rate of 20 nL/h.

Analysis of the reactor exit gas was carried out by the following method.

1. Oxygen

Using the absolute calibration curve method, 50 ml of efflux gas was sampled and the total amount was directed into the 1 ml gas sampler of a gas chromatograph for analysis under the following conditions.

Gas chromatograph: Shimadzu gas chromatography gas sampler (MGS-4: 1 ml metering tube)-equipped gas chromatograph (GC-14 (B) by Shimadzu Corp.)
Column: MS-5A IS 60/80 mesh (3 mmΦ×3 m)
Carrier gas: helium (flow rate: 20 ml/min)
Temperature conditions: Detector temperature and vaporizing chamber temperature: 110° C., column temperature: 70° C., fixed.
Detector: TCD (He pressure: 70 kPaG, Current: 100 m (A))

2. Acetic Acid

Using the internal standard method, 1 ml of 1,4-dioxane was added as an internal standard to 10 ml of reaction solution to prepare a solution for analysis, and 0.2 μl thereof was injected and analyzed under the following conditions.
Gas chromatograph: GC-14B by Shimadzu Corp.
Column: Thermon 3000 packed column (length: 3 m, inner diameter: 0.3 mm)
Carrier gas: Nitrogen (flow rate: 20 ml/min)
Temperature conditions: Detector temperature and vaporizing chamber temperature: 180° C., column temperature: 50° C. maintained for 6 minutes from start of analysis, increased to 150° C. thereafter at a temperature-elevating rate of 10° C./min, and held at 150° C. for 10 minutes.
Detector: FID ($H_2$ pressure: 40 kPaG, air pressure: 100 kPaG)

3. Vinyl Acetate

Using the internal standard method, 1 g of n-propyl acetate was added as an internal standard to 6 g of reaction solution to prepare a solution for analysis, and 0.3 μl thereof was injected and analyzed under the following conditions.
Gas chromatograph: GC-9A by Shimadzu Corp.
Column: TC-WAX capillary column (length: 30 m, inner diameter: 0.25 mm, film thickness: 0.5 μm)
Carrier gas: Nitrogen (flow rate: 30 ml/min)
Temperature conditions: Detector temperature and vaporizing chamber temperature: 200° C., column temperature: 45° C. maintained for 2 minutes from start of analysis, increased to 130° C. thereafter at a temperature-elevating rate of 4° C./min, held at 130° C. for 15 minutes, increased to 200° C. thereafter at a temperature-elevating rate of 25° C./min, and held at 200° C. for 10 minutes.
Detector: FID ($H_2$ pressure: 60 kPaG, air pressure: 100 kPaG)

Sampling was performed at 4 hours after start of the reaction and the initial activity of the catalyst was measured. The evaluation results are shown in Table 1.

TABLE 1

| Catalyst | Example Comp. Ex. | Step order *1 | Solution ratio (mass equivalents) *2 | Vinyl acetate activity (g/L-cat · h) | Vinyl acetate selectivity (%) |
|---|---|---|---|---|---|
| Catalyst A | Example 1 | 1→2 | 3.0 | 784 | 92 |
| Catalyst B | Example 2 | 1→2 | 3.0 | 948 | 91 |
| Catalyst C | Comp. Ex. 1 | 2→1 | 3.0 | 746 | 90 |
| Catalyst D | Comp. Ex. 2 | 2→1 | 3.0 | 820 | 91 |
| Catalyst E | Example 3 | 1→2 | 3.0 | 955 | 92 |
| Catalyst F | Example 4 | 1→2 | 3.0 | 867 | 92 |
| Catalyst G | Example 5 | 1→2 | 3.0 | 905 | 91 |
| Catalyst H | Example 6 | 1→2 | 3.0 | 734 | 92 |
| Catalyst I | Comp. Ex. 3 | 1→2 | 1.0 | 715 | 91 |
| Catalyst K | Comp. Ex. 5 | 2→1 | 3.0 | 842 | 91 |
| Catalyst L | Comp. Ex. 6 | 2→1 | 3.0 | 806 | 91 |
| Catalyst M | Example 7 | 1→2 | 3.0 | 906 | 90 |
| Catalyst N | Example 8 | 1→2 | 3.0 | 868 | 92 |
| Catalyst O | Example 9 | 1→2 | 3.0 | 964 | 91 |

*1: Step 1: Impregnation of catalyst with alkali solution Step 2: Impregnation of catalyst by contact with solution A
*2: (alkali solution + solution A)/carrier absorption Initial Catalytic Activity Evaluation Test B After diluting 5 cc of the catalyst with 20 cc of a silica carrier loading 40 g/L of potassium acetate, it was packed into a reaction tube. Reaction was conducted with a reaction temperature of 150° C., a reaction pressure of 0.6 MPaG, and with a flowing gas with a gas composition of $C_2H_4/O_2/H_2O/HOAc/N_2$=60/4/1.3/17/17.7 (mol %) at a flow rate of 45 nL/h.

The reactor exit gas was analyzed by the same procedure as for the initial reaction activity evaluation A. The initial activity evaluation results for the catalyst are shown in Table 2.

TABLE 2

| Catalyst | Example Comp. Ex. | Step order *1 | Solution ratio (mass equivalents) *2 | Vinyl acetate activity (g/L-cat · h) | Vinyl acetate selectivity (%) |
|---|---|---|---|---|---|
| Catalyst A | Example 1 | 1→2 | 3.0 | 705 | 93 |
| Catalyst B | Example 2 | 1→2 | 3.0 | 833 | 93 |
| Catalyst J | Comp. Ex. 4 | 1→2 | 3.0, dry | 247 | 93 |

*1, *2: Same as Table 1

Initial Catalytic Activity Evaluation Test C

After diluting 15 cc of the catalyst with 60 cc of a silica carrier loading 40 g/L of potassium acetate, it was packed into a reaction tube in the same manner as the one used for evaluation test A. Reaction was conducted with a reaction temperature of 150° C., a reaction pressure of 0.4 MPaG, and with a flowing gas with a gas composition of $C_2H_4/O_2/H_2O/HOAc/N_2$=47.3/6.1/5.6/26.3/14.7 (mol %) at a flow rate of 75 nL/h.

The reactor exit gas was analyzed by the same procedure as for the initial reaction activity evaluation A. The results of evaluating the initial activity of the catalyst (the value at 4 hours after start of the reaction) are shown in Table 3.

TABLE 3

| Catalyst | Example Comp. Ex. | Vinyl acetate activity (g/L-cat · h) | Vinyl acetate activity (%) |
|---|---|---|---|
| Catalyst E | Example 3 | 957 | 91 |
| Catalyst P | Comp. Ex. 7 | 861 | 93 |

Test of Catalytic Activity Reduction after Prolonged Reaction

After diluting 15 cc of the catalyst with 60 cc of a silica carrier supporting 40 g/L of potassium acetate, it was packed into a reaction tube in the same manner as the one used for evaluation test A. Reaction was conducted with a reaction temperature of 150° C., a reaction pressure of 0.4 MPaG, and with a flowing gas with a gas composition of $C_2H_4/O_2/H_2O/HOAc/N_2$=47.3/6.1/5.6/26.3/14.7 (mol %) at a flow rate of 75 nL/h. The catalyst performance at approximately 700 hours after start of the reaction is shown in Table 4.

TABLE 4

| Catalyst | Example Comp. Ex. | Reation time h | Vinyl acetate Activity (STY) g/L-cat · h | Vinyl acetate Selectivity % |
|---|---|---|---|---|
| Catalyst B | Example 2 | 694 | 450 | 94 |
| Catalyst D | Comp. Ex. 2 | 715 | 413 | 93 |

EXAMPLE 10

Preparation of Catalyst Q (Alkali Solution+Solution A at 3.0 Equivalents)

A silica spherical carrier (sphere diameter: 5 mm, specific surface area: 155 m$^2$/g, water absorption: 0.85 g/g, HSV-I by Shanghai Kaigen) was used to prepare a catalyst by the following procedure.

Step 1. A carrier (23 g, amount of water absorption: 19.6 g) was impregnated with an aqueous solution containing 1.97 g of $Na_2SiO_3.9H_2O$, in an amount corresponding to the amount of water absorption of the carrier (1 equivalent). The vessel containing the carrier and aqueous solution was gently shaken for thorough impregnation of the solution.

Step 2. The carrier obtained in step 1 was then immersed in an aqueous solution containing 1.5 g of a 56 mass % $Na_2PdCl_4$ aqueous solution, 1.9 g of $BaCl_2.2H_2O$ and 1.5 g of 17 mass % $HAuCl_4$, in an amount of twice the amount of water absorption of the carrier, and was then allowed to stand for 20 hours.

Step 3. To the aqueous solution of step 2 there was added 3.3 ml of a 52 mass % hydrazine hydrate aqueous solution, and after gentle mixing, the mixture was allowed to stand at room temperature for 4 hours.

Step 4. The palladium/gold/carrier composition was continuously washed with water until complete elimination of chloride ion in the washing water. The washed palladium/gold/carrier composition was dried at approximately 110° C. for 4 hours.

Step 5. The palladium/gold/carrier composition was impregnated with an aqueous solution containing 2 g of potassium acetate, in an amount corresponding to the amount of water absorption of the carrier, and then dried at 110° C. for 4 hours.

COMPARATIVE EXAMPLE 8

Preparation of Catalyst R (Alkali Solution+Solution A at 2.9 Equivalents)

The procedure of Example 10 was repeated, except for impregnation of an aqueous solution containing 1.97 g of $Na_2SiO_3.9H_2O$, in an amount of 0.9 times the amount of water absorption of the carrier, in Step 1.

COMPARATIVE EXAMPLE 9

Preparation of Catalyst S (Alkali Solution+Solution A at 3.0 Equivalents, Drying Step Between Step 1 and Step 2)

The procedure of Example 2 was repeated, but between Step 1. and Step 2. the mixture was allowed to stand at room temperature for 4.5 hours for drying of the carrier to 0.9 times the amount of water absorption.

Initial Catalytic Activity Evaluation Test D

The initial activity of the catalyst was evaluated 4 hours after start of the reaction by the same procedure as the initial catalytic activity evaluation A. The results are shown in Table 5.

Example 10 and Comparative Example 8, which had different alkali solution volumes, show that low alkali solution volumes lower the activity. When Example 2 and Comparative Example 9 are compared, it is seen that the activity is lowered by reducing the solution volume by the drying step after loading of the alkali solution.

TABLE 5

| Catalyst | Example Comp. Ex. | Reaction time h | Vinyl acetate Activity (STY) g/L-cat · h | Vinyl acetate Selectivity % |
|---|---|---|---|---|
| Catalyst Q | Example 10 | 4 | 947 | 91 |
| Catalyst R | Comp. Ex. 8 | 4 | 888 | 91 |
| Catalyst B | Example 2 | 4 | 948 | 91 |
| Catalyst S | Comp. Ex. 9 | 4 | 832 | 90 |

INDUSTRIAL APPLICABILITY

The invention is industrially useful because it can provide a catalyst for alkenyl acetate production with excellent initial activity and selectivity.

The invention claimed is:

1. A process for production of a catalyst for alkenyl acetate production, where the catalyst consists of at least (a) a carrier, (b) palladium or platinum, (c) a Group 11 element and (d) an acetic acid salt, the process comprising:
    1. a step of impregnating a carrier with an alkali solution,
    2. a successive step without drying of further impregnating the carrier by contact with a solution A comprising at least a compound containing palladium or platinum and a compound containing a Group 11 element,
    3. a step of reduction treatment and
    4. a step of loading an acetic acid salt on the carrier,
    and the process being characterized in that in the first step, the carrier is impregnated with an alkali solution having a mass of greater than 0.9 times and no greater than 1.0 times the amount of water absorption of the carrier, after which in the second step it is contacted with solution A to form a catalyst precursor, and in that the total amount of the alkali solution and solution A is a mass of at least 1.5 times and no greater than 8.0 times the amount of water absorption of the carrier.

2. The process for production of a catalyst for alkenyl acetate production according to claim 1, where the catalyst consists of at least (a) a carrier, (b) palladium or platinum, (c) a Group 11 element, (d) an acetic acid salt and (e) an alkaline earth metal element, the process being characterized in that solution A further dissolves a compound containing the (e) alkaline earth metal element.

3. The process for production of a catalyst for alkenyl acetate production according to claim 1, wherein the (b) palladium or platinum is palladium.

4. The process for production of a catalyst for alkenyl acetate production according to claim 1, wherein the (c) Group 11 element is gold or copper.

5. The process for production of a catalyst for alkenyl acetate production according to claim 2, wherein the (e) alkaline earth metal element is at least one from among barium, strontium, magnesium and calcium.

6. A process for production of alkenyl acetates using lower olefins, oxygen and acetic acid as starting materials, the process being characterized by using a catalyst produced by a process according to claim 1.

7. A process for production of vinyl acetate using ethylene, oxygen and acetic acid as starting materials, the process being characterized by using a catalyst produced by a process according to claim 1.

8. A process for production of allyl acetate using propylene, oxygen and acetic acid as starting materials, the process being characterized by using a catalyst produced by a process according to claim 1.

9. The process for production of a catalyst for alkenyl acetate production according to claim 1, wherein the total amount of the alkali solution and solution A is a mass of at least 3.0 times and no greater than 8.0 times the amount of water absorption of the carrier.

* * * * *